United States Patent
Van Patten

(10) Patent No.: US 11,696,894 B2
(45) Date of Patent: Jul. 11, 2023

(54) SEQUENTIAL ADMINISTRATION OF PARTITIONED ABSORPTION ASPIRIN OR ACTIVE ASPIRIN DERIVATIVE AND COX-2 INHIBITOR

(71) Applicant: Peter Van Patten, Aurora, MN (US)

(72) Inventor: Peter Van Patten, Aurora, MN (US)

(73) Assignee: Celsprin LLC, Aurora, MN (US)

( * ) Notice: Subject to any disclaimer, the term of this patent is extended or adjusted under 35 U.S.C. 154(b) by 283 days.

(21) Appl. No.: 14/571,781

(22) Filed: Dec. 16, 2014

(65) Prior Publication Data

US 2015/0164818 A1    Jun. 18, 2015

Related U.S. Application Data

(60) Provisional application No. 61/916,986, filed on Dec. 17, 2013.

(51) Int. Cl.

| | | |
|---|---|---|
| *A61K 9/50* | (2006.01) | |
| *A61K 31/616* | (2006.01) | |
| *A61K 31/60* | (2006.01) | |
| *A61K 45/06* | (2006.01) | |
| *A61K 31/606* | (2006.01) | |
| *A61K 31/635* | (2006.01) | |

(52) U.S. Cl.
CPC ............ *A61K 9/5084* (2013.01); *A61K 31/60* (2013.01); *A61K 31/606* (2013.01); *A61K 31/616* (2013.01); *A61K 31/635* (2013.01); *A61K 45/06* (2013.01)

(58) Field of Classification Search
CPC .................................................. A61K 31/616
See application file for complete search history.

(56) References Cited

U.S. PATENT DOCUMENTS

| | | | | |
|---|---|---|---|---|
| 2003/0143271 A1* | 7/2003 | Ewing | ..................... | A61K 45/06 424/468 |
| 2003/0207846 A1* | 11/2003 | MacMillan | ............ | A61K 45/06 514/161 |
| 2003/0212050 A1 | 11/2003 | Van Patten | | |
| 2007/0154542 A1* | 7/2007 | Tananbaum | ......... | A61K 9/0056 424/457 |
| 2010/0009005 A1* | 1/2010 | Soula | ..................... | A61K 31/60 424/497 |
| 2010/0233272 A1* | 9/2010 | Appel | .................... | A61K 9/146 424/489 |

OTHER PUBLICATIONS

Alvarez-Fuentes et al., "Development of Enteric-coated Timed-release Matrix Tablets for Colon Targeting," Journal of Drug Targeting, Oct.-Dec. 2004 vol. 12 (9-10), pp. 607-612.

Homar et al., "Preparation and evaluation of celecoxib-loaded microcapsules with self-microemulsifying core," Journal of Microencapsulation, 2009; 26(6):479-484.

Kanthamnen et al., "Nanoparticulate delivery of novel drug combination regiments for the chemoprevention of colon cancer," Int J Oncol, Jul. 2010: 37(1): 177-185.

Lichtenberger et al., "Association of Phosphatidylcholine and NSAIDS as a Novel Strategy to Reduce Gastrointestinal Toxicity," Drugs of Today 2009, 45(12): 877-890.

Lin et al., "Tablet formulation study of spray-dried sodium diclofenac enteric-coated microcapsules," Pharm Res. Jul. 1991; 8(7):919-24.

Morgen et al., "Polymeric Nanoparticles for Increased Oral Bioavailability and Rapid Absorption Using Celecoxib as a Model of a Low-Solubility, High-Permeability Drug," Pharm Res. Feb. 2012; 29(2): 427-440.

Paulson et al., "Pharmacokinetics of Celecoxib after Oral Administration in Dogs and Humans: Effect of Food and Site of Absorption," The Journal of Pharmacology and Experimental Therapeutics, vol. 297, No. 2 (2001).

Sengel et al., "Preparation and in vitro evaluation of meloxicam-loaded PLGA nanoparticles on HT-29 human colon adenocarcinoma cells," Drug Dev Ind Pharm. Sep. 2012; 38(9):1107-16.

Zaid et al., "Development and stability evaluation of enteric coated Diclogenac sodium tablets using Sureteric," Pak. J. Pharm. Sci., vol. 25, No. 1, Jan. 2012, pp. 59-64.

"An Update on Pharmaceutical Film Coating for Drug Delivery," Felton & Porter, Expert Opin. Drug Deliv. (2013) 10 (4) 2013.

"Raman and Thermal Analysis of Indomethacin/PVP Solid Dispersion Enteric Microparticles," Fini et. al., Eur. Jour. Pharm. & Biopharm. 70 (2008) 409-420.

"Albumin Microspheres as Carriers for the Antiarthritic Drug Celecoxib," Thakkar et al., AAPS Pharm. Sci. Tech. 2005; 6 (1) Art. 12.

"Development of Spray-Dried Co-Precipitate of Amorphous Celecoxib Containing Storage and Compression Stabilizers," Dhumal et al., Acta Pharm. 57 (2007) 287-300.

"Enteric Coated HPMC Capsules Designed to Achieve Intestinal Targeting," Cole et. al., Int. Jour. Pharm. col. 231, Issue 1, p. 83-95 (2002).

"The Formulation of Flurbiprofen Loaded Microspheres Using Hydroxypropylmethylcellulose and Ethylcellulose," Shahzad et. al., Adv. Clin. Exp. Med. 2013 22, 2, 177-183.

"Formulation and Evaluation of Stable Modified Release Tablets of Tramadol Hydrochloride with Bi-Phasic Release Model," Maram et. al., Int. Jour. Pharm. Sci. Rev. & Res. vol. 13, Issue 2, Mar.-Apr. 2012.

(Continued)

*Primary Examiner* — Melissa L Fisher
(74) *Attorney, Agent, or Firm* — Kagan Binder, PLLC

(57) ABSTRACT

Described herein are an aspirin or active aspirin derivative and a COX-2 inhibitor, at least one of which has an enteric or partial enteric coating, administered in combination yet delivered sequentially, for the treatment and prophylactic treatment of diseases, symptoms and conditions. In some embodiments, the COX-2 inhibitor has the enteric coating; however, the aspirin or active aspirin derivative may additionally or alternately have the enteric coating. In all embodiments, the drug having the enteric coating or enteric formulation is targeted for absorption in the small intestine or colon, or both the small intestine and the colon.

12 Claims, No Drawings

(56) References Cited

OTHER PUBLICATIONS

"Nanoparticle-Based Topical Opthalmic Formulations for Sustained Celecoxib Release," Ibrahim et. al., Jour. Pharm. Sci., vol. 102, No. 3, Mar. 2013.
"Polymeric Micelles for Oral Drug Delivery," Gaucher et. al., Eur. Jour. Pharm. & Biopharm. 76 (2010) 147-158.
"Oral Drug Delivery Systems Using Chemical Conjugates or Physical Complexes," Al-Hilal et. al., Adv. Drug Del. Rev., 65 (2013) 845-864.
"Encapsulation of Lipophilic Drug within Enteric Microparticles by a Novel Coacervation Method," Dong & Bodmeier, Int. Jour. Pharm., col. 326, Issues 1-2, p. 128-138 (2006).
"Formulation and Evaluation of Albumin Microspheres and its Enteric Coating Using a Spray-Dryer," Bejugam et. al., Jour. Microencapsulation, Dec. 2008: 25(8): 577-583.
"Microcapsules Formulated in the Enteric Coating Copolymer Endragit L100 as Delivery Systems for Oral Vaccination against Infections by Gastrointestinal Nematode Parasites," Dea-Ayuela et. al., Jour. Drug Targeting, Sep. 2006; 14(8): 567-575.
"Pharmaceutical Approaches to Colon Targeted Drug Delivery Systems," Chourasis & Jain, Jour. Pharm. Sci. 6(1):33-66 (2003).
Paulson, et al., "Pharmacokinetics of Celecoxib after Oral Administration in Dogs and Humans: Effect of Food and Site of Absorption," The Journal of Pharmacology and Experimental Therapeutics, vol. 297, No. 2, 8 pages, 2001.

\* cited by examiner

SEQUENTIAL ADMINISTRATION OF PARTITIONED ABSORPTION ASPIRIN OR ACTIVE ASPIRIN DERIVATIVE AND COX-2 INHIBITOR

REFERENCE TO RELATED APPLICATION

This application claims the benefit of U.S. Provisional Application 61/916,986, filed Dec. 17, 2013, the entire disclosure of which is hereby incorporated by reference.

TECHNICAL FIELD

The present invention relates to prophylactic or targeted prophylactic treatment of diseases and conditions, as well as compositions for prophylactic or targeted treatment of diseases and conditions.

Examples of diseases and conditions that can be treated by short-term administration include acute pain, fever, dysmenorrhea, acute migraine, prevention of migraine in a time window, and prevention of intra-abdominal adhesions. Examples of diseases and conditions that can be treated by long-term administration include osteoarthritis, other arthritides, subacute and chronic pain, prophylaxis of subacute or chronic migraine, cancer prevention, cancer treatment, and prevention or treatment of pre-cancerous intestinal (colon or rectal) polyps, and familial adenomatous polyposis (FAP).

BACKGROUND

It is advantageous to have a drug formulation that can deliver two different compounds separated by a significant period of time. A drug formulation comprising aspirin and an NSAID (non-steroidal anti-inflammatory drug) may be delivered separated by a significant period of time. Alone, aspirin appears to be rapidly absorbed in the stomach and the small intestine and also in the colon. Alone, COX-2 inhibitors have poor solubility in humans, and therefore cause a slow absorption in the small intestine (Chourasis & Jain, J. Pharm. Sci., Vol. 6, p. 33-36). It would be advantageous to combine a COX-2 inhibitor and an aspirin derivative to deliver the COX-2 inhibitor in a form that encourages rapid absorption and the aspirin or aspirin active derivative's release is delayed.

COX-2 inhibitors are predominantly BCS Class II molecules, meaning the bioavailability of the compound is limited by their solvation rate. Recently, COX-2 inhibitors have been formulated in ways to enhance solubility and increase the rate of absorption. One way to enhance solubility relies on COX-2 inhibitors high lipophilicity and uses lipid based systems to administer the compound (Homar et. at., J. Microencaps, Vol. 29, p. 479-484; Thakkar et. al., AAPS Pharm. Sci. Tech., Vol. 6, Art. 12, p. E65-E73). Another approach is to add bile salts to the COX-2 inhibitor (Morgen et. al., Pharm. Res. Vol. 29, p. 427-440). The addition of bile salts provides a significant increase in the dissolution rate and a commensurate increase in the rate of absorption. Yet another approach is to use COX-2 inhibitor conjugates (Al-Hilal et. al., Adv. Drug Delivery Rev. Vol. 65, p 845-864).

A more useful approach to increase solubility has been determined. The solubility characteristics of spray dried amorphous dispersions of drugs are enhanced (Fini et. al., Eur. J. Pharm. & Biopharm., Vol. 70, p 409-420; Dhumal et. al., Acta. Pharmaceutica, Vol. 57, p. 287-300). Celeboxib (the commercial name of a COX-2 inhibitor) and a combination of PVP (alpha-Pyrrolidinopentiophenone) and Carageenan suggest a synergistic action of two polymers to stabilize the material after compaction (Dhumal). The use of spray dried dispersions of poorly soluble drugs to improve solubility and shorter $T_{max}$ and higher $C_{max}$ values of the crystalline form of the drug is well known. Spray dried dispersions have a limited cost and limited regulatory issues.

In some embodiments, a delayed release of drugs is desired, while in other embodiments, a several hour delay between immediate release of drugs is desired. Other embodiments desire to slow the release of drugs from a dosage form. These technologies provide a steady release of a drug along the gastrointestional tract in order to minimize the drug's $C_{max}$ (see i.e., Shahzad et. al., Adv. Clin. Expt. Med., Vol. 22, p 177-183; Gaucher et. al. Eur. J. Pharmaceutics & Biopharm., Vol. 76, p. 147-158; Bejugam et. al., J. of Microencapsulation, Vol. 25, p. 577-583; Dea-Ayuela et. al., Drug Targeting, Vol. 14, p. 567-575). A steady release also reduces the probability of side effects and extends the blood levels of the drug.

In contrast, it may be more advantageous to provide a "burst" release of the drug (Alvarez-Fuentes et. al., J. Drug Targeting, Vol. 12, p. 607-612; Cole et. al., Int. J. Pharmaceutics, Vol. 231, p. 83-95). For example, an immediate release of a COX-2 inhibitor at a specific time after dosing may be desired.

A system used to provide a timed release of a drug utilizes an enteric coated matrix (Alvarez-Fuentes). This also slowed the subsequent release of the drug, which can be effected by the presence of other inert materials. HPMC capsules (hydroxypropyl methylcellulose) may also be enteric coated (Cole). The in-vivo gamma scintigraphy data shows that enteric coated HPMC capsules may provide a controlled delivery. Potential enteric coatings may be Eudragit® or Caps Canada, which enables the drug to be absorbed in specific areas of the intestine. An additional layer of immediate release drug prepared as a spray dried dispersion (for rapid dissolution) would provide a biphasic release.

The process of combining an immediate and delayed release mechanism into one simple biphasic release product is advantageous (Maram et. al., Int. J. Pharm. Sci., Vol. 13, p. 116-120). For example, a complex, compression coated formulation of Tramado was mimicked using a spray coating process (Maram). No matter how the drug is coated, the enteric coating must be a high quality (Zaid & Qaddomi, Pakistan J. of Pharmaceutica, Vol. 25, p. 59-64; Felton & Porter, Expert Opin. On Drug Delivery, Vol. 10, p. 421-435). An adaptation of the Maram approach would be to replace the compression coating with a spray coated nanoparticulate COX-2 inhibitor such as celecoxib or celecoxib analogue.

SUMMARY OF THE INVENTION

One particular embodiment of this disclosure is a method of sequentially administering an aspirin or active aspirin derivative and a COX-2 inhibitor for partitioned absorption, at least one of which has an enteric or partial enteric coating for bioabsorption in a patient's small intestine or colon.

In one embodiment, the present invention provides a method for sequentially administering an aspirin or active aspirin derivative and a COX-2 inhibitor for partitioned absorption, at least one of which has an enteric or partial enteric coating for bioabsorption in a patient's small intestine or colon. The COX-2 inhibitor and the aspirin or the aspirin derivative may have an enteric or partial enteric coating. The method may be for the treatment of diseases and conditions where bioabsorption in the small intestine is desired or where bioabsorption in the colon is desired. The administration of the aspirin or active aspirin derivatives and the COX-2 inhibitor may be long-term, short-term, or may be periodic.

In another embodiment, the present invention provides a method for the treatment of diseases and conditions such as osteoarthritis, other arthritides, subacute and chronic pain, prophylaxis of subacute or chronic migraines, cancer prevention, cancer treatment, and prevention or treatment of pre-cancerous intestinal (colon or rectal) polyps, and familial adenomatous polyposis (FAP). The method may also be for the treatment of diseases and conditions including dysmenorrhea, prevention of dysmenorrhea, menstrual or pen-menstrual migraines, prevention of menstrual or peri-menstrual migraines, prevention or treatment of dysmenorrhea and menstrual or pen-menstrual migraines in patients with both conditions, and prevention or treatment of migraines in a patient with recurring time windows where there is a need to be free of migraine symptoms during the time windows. The method may also be for the treatment of diseases and conditions including acute pain, fever, dysmenorrhea, acute migraine, prevention of migraine in a time window, or prevention of intro-abdominal adhesions.

The aspirin or active derivative of aspirin of the present method may comprise at least one of ASA, PC-ASA, PL2200, PA8140, and PA32540. The COX-2 inhibitor of the method may comprise celecoxib, celecoxib analogue, PC-celecoxib, or a PC-celecoxib analogue.

In yet another embodiment, the method includes providing a coating that is pH-sensitive, time-sensitive, and/or microflora-activated.

In still yet another embodiment, a kit comprising an aspirin or active aspirin derivative and a COX-2 inhibitor, at least one of which has an enteric or partial enteric coating is provided. The COX-2 inhibitor may have an enteric or partial enteric coating. The aspirin or active aspirin derivative may have an enteric or partial enteric coating.

Another particular embodiment of this disclosure is a kit comprising an aspirin or active aspirin derivative and a COX-2 inhibitor, at least one of which has an enteric or partial enteric coating.

Yet another embodiment of this disclosure is an empty or partially empty kit. The kit may contain the ASA or active derivation, allowing a user to add the COX-2 inhibitor, or the kit may contain the COX-2 inhibitor, allowing a user to add the ASA or active derivation. The COX-2 inhibitor may have an enteric or partial enteric coating or a time-sensitive coating. The aspirin or active aspirin derivative may have an enteric or partial enteric coating or a time-sensitive coating.

These and various other features and advantages will be apparent from a reading of the following detailed description.

DETAILED DESCRIPTION OF THE INVENTION

The present embodiments are directed to use of, in combination yet delivered sequentially, an aspirin or active aspirin derivative and a COX-2 inhibitor, at least one of which has an enteric or partial enteric coating. The aspirin component may be a combination of two or more aspirin or active aspirin derivatives, at equal or unequal portions. The aspirin or active aspirin derivative and a COX-2 inhibitor combination is used for treatment and prophylactic treatment of diseases, symptoms and conditions where partial or complete bioabsorption in the small intestine or colon of at least one component is desired in order to reduce GI side effects. In some embodiments, the COX-2 inhibitor has the enteric coating. In alternative embodiments, the aspirin or active aspirin derivative has the enteric coating for embodiments where small intestinal or colonic targeting is desired. In all embodiments, an enteric coating or enteric formulation means the drug release is targeted for absorption in the small intestine or colon, or both the small intestine and the colon, rather than in the stomach.

The drug combination, when administered in combination yet delivered sequentially or at offsetting time periods, is particularly suited for treating chronic inflammation that interferes with function (and that is generally targeted by COX-2 inhibitors) in the moveable bony joints, cartilage, and proximate soft tissue areas. The drug combination is also suited for other conditions such as migraine, dysmenorrhea, prevention of pre-cancerous polyps with or without familial adenomatous polyposis (FAP), prevention of cancer, treatment of cancer, and prevention of post-surgical adhesions, in which the target tissue is generally thought to be in a soft tissue location other than moveable bony joints, cartilage, and proximate soft tissue areas. For example, with respect to migraine a possible target tissue is the perivascular tissue on the surface of the brain that is close to the skull but not close to moving joints. Inflammation or neurotransmitter modulation within the brain is another possible target of the drug combination for migraine treatment (or other brain disorders such as mood disorders or schizophrenia).

In all embodiments, the aspirin or active derivative of aspirin (for example phosphatidylcholine treated aspirin or PC-ASA, PL2200 available PLx Pharma Inc, Houston, Tex., or PA8140 and PA32540 both available from Pozen Inc, Chapel Hill, N.C.) has an anti-platelet effect whether the formulation is non-enteric, enteric, or partially enteric. The COX-2 inhibitor, such as celecoxib, celecoxib analogue, phosphatidylcholine treated celecoxib or PC-celecoxib, or phosphatidylcholine treated celecoxib analogue or PC-celecoxib analogue, does not have an anti-platelet effect whether the formulation is non-enteric, enteric or partially enteric.

The use of NSAID drugs has been limited due to the resulting GI side effects (exemplified by aspirin and conventional NSAIDs) and increased cardiovascular risk, which is greater in COX-2 inhibitors but also present when conventional NSAIDS are used. It is not known whether the overall cardiovascular risk associated with NSAIDs would be reduced more if aspirin were to be combined with a COX-2 inhibitor as opposed to a conventional NSAID. Conventional NSAIDs, including aspirin, are known to cause GI side effects and intolerance. An adverse drug interaction has been identified when aspirin and other NSAIDs, including COX-2 inhibitors, are taken together. This adverse interaction may lead to GI erosions, ulceration, and slower healing of existing GI lesions.

Experts have stated that COX-2 inhibitors should not be used in certain conditions, such as the prevention of migraines or migraines, because of an increased cardiovascular risk. The use of celecoxib with aspirin (or active aspirin derivative) for prophylactic treatment of migraines is reported in US Pub No 2003/0212050, the complete disclosure of which is incorporated herein by reference. Others have since proposed combining COX-2 inhibitors with aspirin and/or antioxidant flavonoids.

Lichtenberger, in *Drugs of Today* 2009, 45 (12):877-890, has proposed reducing the GI risk of NSAIDS, including PL2200 which is an active aspirin derivative available from PLx Pharma Inc., by associating the NSAID in a non-covalent bond with a component of soy lecithin (phosphatidylcholine or PC). Lichtenberger proposed a potential clinical use of this phosphatidylcholine coating or PLX technology when a COX-2 inhibitor is prescribed concurrently with aspirin or conventional NSAID. In particular, Lichtenberger stated the PLX active derivative of aspirin (i.e., PC-ASA) may be useful when combined with celecoxib in the setting of a chronic inflammatory disease in patients with known cardiac disease. PC-ASA, when combined with celecoxib, resulted in less rodent GI toxicity than aspirin alone or a combination of celecoxib and ASA. However, this paper also showed the combination reduced, but did not eliminate rodent GI toxicity, when celecoxib and PC-ASA were used together.

In his paper cited above, Lichtenberger refers to "high-risk individuals suffering from chronic inflammatory and cardiac diseases" suggesting a "potential therapeutic role for PC-associated aspirin and perhaps other PC-NSAIDs" in "both the prevention of mucosal injury and treatment of pre-existing ulcers" "when patients are placed on regimens that require the concomitant use of both a Coxib and a conventional NSAID." Lichtenberger also twice refers to a choice other than aspirin or active aspirin derivative: the first time he seems to suggest that a PC-NSAID that is not a derivative of aspirin (and likely not a COX-2 inhibitor) might be useful; and the second time he uses the term "conventional NSAID" which may include many other choices besides aspirin (for example, a PC-NSAID which may or may not have any cardio-protective effect). Overall, Lichtenberger suggests that while providers may currently be forced to used this risky combination for this patient group, in the future providers may consider switching from aspirin to PC-ASA when the patient has cardiac disease and requires a long-term COX-2 inhibitor treatment; alternatively, providers can look at one (or more) of the other PC-NSAID products.

Unlike Lichtenberger's findings, the combination of aspirin or active aspirin derivative and COX-2 inhibitors, according to the present invention, further reduces GI side effects, symptoms and/or toxicity in part by targeting separate areas of the GI tract (for partitioned absorption) when the use of this combination is needed or indicated and also by using separate time windows when needed or indicated. This is accomplished by the present invention by including an enteric coating on at least one of the aspirin or active aspirin derivative and COX-2 inhibitor in order to target bioabsorption, for example, to the colon and small intestine.

There are studies indicating that COX-2 inhibitors have increased cardiovascular risk to a greater extent than traditional NSAIDs even when used for short periods of time. This consideration is even more important if the condition being treated presents an increased cardiovascular risk (e.g., migraine, rheumatoid arthritis).

A need exists for the combination of COX-2 inhibitors (e.g., celecoxib, celecoxib analogue, PC-celecoxib, or PC-celecoxib analogue) and aspirin or active aspirin derivatives (e.g., PC-ASA and PL2200) for short-term use for the following conditions: acute pain, fever, dysmenorrhea, acute migraine, prevention of migraine in a time window, and prevention of intra-abdominal adhesions.

A need exists for longer term use of the combination COX-2 inhibitors (e.g., celecoxib, celecoxib analogue, PC-celecoxib, or PC-celecoxib analogue) and aspirin or active aspirin derivatives (e.g., PC-ASA or PL2200) in the following conditions: osteoarthritis, other arthritides, chronic pain, prophylaxis of chronic migraine, cancer prevention, cancer treatment, and prevention or treatment of pre-cancerous intestinal (colon or rectal) polyps, including use in the setting of familial adenomatous polyposis (PAP).

A need exists for regular periodic or short-term use of the combination of COX-2 inhibitors (e.g., celecoxib, celecoxib analogue, PC-celecoxib, or PC-celecoxib analogue) and aspirin or active aspirin derivatives (e.g., PC-ASA or PL2200) in these conditions: dysmenorrhea, prevention of dysmenorrhea, menstrual or pen-menstrual migraine, prevention of menstrual or peri-menstrual migraine, prevention or treatment of dysmenorrhea and menstrual or pen-menstrual migraine in patients with both conditions, and prevention or treatment of migraine in patients with recurring time windows where there is a need to be free of migraine symptoms during the time windows. A need also exists for acute or subacute pain.

Regardless of whether the celecoxib, celecoxib analogue, PC-celecoxib, or PC-celecoxib analogue and aspirin or active aspirin derivative are taken concomitantly, at different times of the day, or even on alternate days, there still exists the potential for adverse GI drug effects as seen in Lichtenberger's rodent study. This potential increases with the dosage used and longer periods of use and is more likely to derive from local proximity of the GI mucosa to these drugs but may also derive from systemic absorption with subsequent effect on local tissues. The present invention provides an enteric or partially enteric coating on at least one of the celecoxib, celecoxib analogue, PC-celecoxib, or PC-celecoxib analogue and the aspirin or active aspirin derivative for reducing the potential adverse GI drug effects.

Enteric coatings and/or formulations have been used to reduce the GI side effects of various medications, including aspirin and conventional NSAIDs. These coatings and/or formulations have also been proposed for targeted drug delivery within the GI tract (for example, targeted absorption in the colon for treatment of ulcerative colitis). Enteric coatings of aspirin have traditionally been designed to reduce gastric and/or duodenal GI symptoms or side effects, favoring absorption in the small intestine (or distally) with slower onset of action. Traditional (non-enteric) aspirin is absorbed in the gastric and/or duodenal area and has a faster onset of action. The active derivative of aspirin (e.g., PC-ASA or PL2200) has an onset of action stated to be equivalent to traditional (non-enteric) aspirin and is therefore likely absorbed in the gastric and/or duodenal area.

There is a need to further reduce GI side effects of the combination of celecoxib, celecoxib analogue, PC-celecoxib, or PC-celecoxib analogue and the aspirin or active aspirin derivative such as PC-ASA/PL2200 as well as other forms of active aspirin derivatives. Embodiments of this invention that utilize enteric coating/formulation technology for either the celecoxib, celecoxib analogue, PC-celecoxib, PC-celecoxib analogue or PC-ASA/PL2200 accomplish this conveniently with improved compliance. Examples of various enteric coatings for the COX-2 inhibitor and active aspirin derivatives are provided below. These enteric coatings and/or formulations (either partial or complete) are designed to maximize efficacy for the intended clinical purpose while preserving the cardiovascular benefits of low dose aspirin and minimizing GI side effects and/or toxicity.

Suitable enteric coatings include polymethacrylates (methacrylic acid/ethyl acrylate); cellulose ester polymers such as cellulose acetate phthalate or CAP (also known as "Aquateric"), cellulose acetate trimellitate (CAT), hydroxylpropyl methyl cellulose phthalate, and hydroxylpropyl methyl cellulose acetate succinate (HPMC); polyvinyl derivatives such as polyvinyl acetate phthalate or PVAP (also known as "Coateric" and "Sureteric"); methacrylic acid copolymers, and acrylic copolymers. A mixture of sodium alginate and aqueous ammonium salt of shellac is another, "food grade," enteric coating. The enteric coatings may be aqueous-based or solvent-based (e.g., organic solvent-based), and may be present with or without a subcoating. The enteric coating may be, for example, time-sensitive, pH-sensitive, and/or microflora-activated, and may be present in a range of, for example, 10-50 wt % (e.g., 20 wt %, 25 wt %, 30 wt %, 35 wt %, 40 wt %) of the coated drug.

For bioavailability in the small intestine, preferably, the enteric formulations should have less than 10% of drug release after 2 hours in the acid stage, and completion of drug release in the continuation testing in the buffer stage should take place within 45 minutes. Specific examples of suitable enteric coatings include "Eudragrit L 30 D-55" which is a copolymer of methacrylic acid and ethyl acrylate that dissolves at a pH of 5.5, and "Eudragrit L100" which dissolves at a pH above 6 and may be preferable to the "L 30 D-55" product by reducing overlapping release of the COX-2 inhibitor and aspirin (as long as an adequate absorption profile for the celecoxib or ASA component is maintained). Both "Eudragrit L 30 D-55" and "Eudragrit L 100" are available from Evonik Industries AG, Essen, Germany.

Colonic targeting of the COX-2 inhibitor or celecoxib component may require a formulation with improved bioavailability (BA). One alternative is a strategy of colonic targeting by using, for example, microcapsules (which may include a self-emulsifying core) or polymeric and/or non-polymeric nanoparticles of the COX-2 inhibitor or celecoxib component. Once drug release has occurred at the ileal-colonic junction or proximal colon, there would be improved absorption, as compared to the present commercially available product. Alternatively colonic targeting by using an enteric coating of the present commercially available COX-2 inhibitor or celecoxib component would result in acceptable absorption and bioavailability. Examples of enteric formulations include "Eudragrit S 100" and "Eudragrit FS 30 D" which dissolve at a pH below 7.0 making these enteric coatings suitable for colonic targeting (drugs typically released at or near the ileo-cecal junction or proximal colon). Both "Eudragrit S 100" and Eudragrit "FS 30 D" are available from Evonik Industries AG, Essen, Germany. Time-dependent, pro-drug, and microflora-activated systems are also suitable, as well as combinations of pH and time-dependent systems. Nanoparticles of celecoxib may also be useful for non-enteric or partially enteric formulations.

In some embodiments, the aspirin or active aspirin derivative component does not have an enteric coating. For embodiments where the aspirin or active aspirin derivation has an enteric coating, a suitable coating is a polymer type that promotes pH-dependent release. In some embodiments, a taste masking pH-dependent solubility polymer can be used; such a polymer may be a 'reverse enteric' system that is insoluble in the higher pH of the saliva but immediately dissolves in the acidic pH of the stomach.

Enteric coating of the aspirin or active aspirin derivative component (e.g., PC-ASA or PL2200) may be relatively challenging, though possible, as there can be problems with adherence of many enteric coatings and breakdown due to the interface with a gelatin capsule often on the aspirin active derivative component. If the capsule of PC-ASA was HPMC, enteric coating would be relatively straightforward. Capsule-in-capsule technology, if used, requires the enteric coating of the inner capsule to be compatible in terms of shelf life and maintenance of release profile with the product and the carrier located in the intervening space. Examples of such constructions include an inner enteric-coated HPMC capsule with an outer hard gelatin capsule, an inner hard gelatin capsule with an outer enteric-coating HPMC capsule, both inner and outer HPMC capsules, or both inner and outer hard gelatin capsules. An alternative is over-encapsulation (a representative example would include use of the Caps Canada product).

A kit containing the COX-2 inhibitor and aspirin or active aspirin derivative may be very useful for the purpose of patient compliance and to remind patients not to take OTC aspirin or conventional NSAIDs while taking the combination. The use of the kit may contain instructions for taking the active aspirin derivative or aspirin at a different time of day than celecoxib, celecoxib analogue, PC-celecoxib, or PC-celecoxib analogue; or on alternate days, in order to reduce potential side effects of the drugs when taken concomitantly.

Various embodiments of kits include a kit (e.g., "C pack" or "Cel pack" or "Celsprin pack") with separate dosing units where the COX-2 inhibitor such as celecoxib, celecoxib analogue, PC-celecoxib, or PC-celecoxib analogue (partially or fully enteric formulation or non-enteric) and aspirin or active aspirin derivative such as ASA, PC-ASA, or PL2200 (partially or fully enteric formulation or non-enteric) are taken separately, or alternatively a kit with a single dosage unit which may include capsule-in capsule technology or other formulations where: either the celecoxib, celecoxib analogue, PC-celecoxib, or PC-celecoxib analogue is a non-enteric formulation and the aspirin or active aspirin derivative is a partially or fully enteric formulation in the same dosage unit; or the celecoxib, celecoxib analogue, PC-celecoxib, or PC-celecoxib analogue is a partially or fully enteric formulation and the PC-ASA/PL2200 is a non-enteric formulation in the same dosage unit. Partially enteric formulation may be capsule-in-capsule or other partially enteric formulation.

Dosages of the COX-2 inhibitor and aspirin or aspirin derivative may have a tablet size of about 600 mg comprising about 200 mg of the active ingredients. In an example embodiment, the table may contain about 150 mg of a COX-2 inhibitor and 50 mg of an aspirin or aspirin derivative. Other example embodiments may include 119 mg COX-2 inhibitor and 81 mg aspirin or aspirin derivative, or 125 mg COX-2 inhibitor and 75 mg aspirin or aspirin derivative.

Dosages of the celecoxib component would be in the range of 50-400 mg per day, most typically 200 mg per day (or 100 mg twice daily) for chronic conditions such as osteoarthritis (a formulation with increased bioavailability may require fewer mg per day). Elderly patients may do well on a smaller dose (for example, 100 mg per day) for similar conditions. In dysmenorrhea and acute pain studies for Celebrex, 400 mg was given initially followed by an additional 200 mg if needed, then 200 mg once every 12 hours for several days. Treatment of acute migraine, or acute migraine with dysmenorrhea, would be similar in dosing level to dysmenorrhea (acute pain) dosing.

The recommended dose of celecoxib for familial adenomatous polyposis (FAP) is 400 mg twice daily. This dose could be lowered in some patients (e.g., for FAP, colon CA prevention and/or treatment; prevention of pre-cancerous polyps) if the aspirin component is given concomitantly (celecoxib component in a range of 200-800 mg per day, for example). For prevention of intra-abdominal adhesions, a dose of 100-400 mg per day for the celecoxib component is useful. Most guidelines for celecoxib stress use of the lowest effective dose for the condition being treated.

Prophylactic treatment of menstrual migraine may require treatment for 5-15 days per cycle and would likely be in the range of 200-400 mg per day, and possibly down to 100 mg per day, if there are tolerability issues.

For the aspirin component, the dose for acute migraine or acute pain (or dysmenorrhea) can be as high as 1,200 mg but more typically it would be in a range of 300-650 mg, 75-325 mg, or in the range of 50-650 mg, when combined with the celecoxib component. For familial adenomatous polyposis (FAP) and similar conditions, a typical dose for the aspirin component would be 162-325 mg per day, or in the range of 50-500 mg per day.

Aspirin and aspirin derivative doses for prophylaxis of migraine can be found in U.S. Pub. No. 2003/0212050. Typically, the aspirin component would be 81, 162, or 325 mg for the PL2200 active aspirin derivative and 81, 100, 162, 200, or 325 mg for the PA8140 and PA32540 active aspirin derivatives (dose range of 40-500 mg). The dose range would be similar for chronic conditions (e.g., 40-325 mg daily, or 162-500 mg every other day).

For prevention of intra-abdominal adhesions, a typical dose would be 50-162 mg per day (range 40-325 mg per day) for the aspirin or active aspirin derivative component.

In another embodiment, the celecoxib, celecoxib analogue, PC-celecoxib, or PC-celecoxib analogue is a partially or fully enteric formulation and given as a single dosage unit which may or may not be combined with non-enteric aspirin or certain non-enteric active derivatives of aspirin (e.g., PC-ASA, PL2200, PA8140, or PA32540) taken separately or in a kit). Partial enteric formulation may be capsule-in-capsule or other partially enteric formulation.

An embodiment exists where the ASA or PC-ASA is a partially or fully enteric formulation and is given as a single dosage unit which may or may not be combined with a non-enteric celecoxib, celecoxib analogue, PC-celecoxib, or PC-celecoxib analogue separately or in a kit. Partially enteric formulation may be capsule-in-capsule or other partially enteric formulation.

An embodiment exists where the ASA or PC-ASA/PL2200 and the celecoxib, celecoxib analogue, PC-celecoxib, or PC-celecoxib analogue are either both in a partially enteric formulation or both in a fully enteric formulation targeted to the small intestine or colon (or both the small intestine and colon).

An embodiment exists where the ASA or PC-ASA/PL2200 is in a partially enteric formulation and the celecoxib, celecoxib analogue, PC-celecoxib, or PC-celecoxib analogue is in a fully enteric formulation targeted to the small intestine, colon, or both areas.

An embodiment exists where the celecoxib, celecoxib analogue, PC-celecoxib, or PC-celecoxib analogue is in a partially enteric formulation and the ASA or PC-ASA is in a fully enteric formulation targeted to the small intestine, colon, or both areas.

In embodiments containing a partially enteric formulation, it is expected that some portion of the formulation will be absorbed in the gastric and/or duodenal areas of the intestine and the remainder of the formulation will be targeted to the small intestine, colon, or both the small intestine and colon.

An embodiment exists where the celecoxib, celecoxib analogue, PC-celecoxib, or PC-celecoxib analogue is in a rectal suppository formulation with or without aspirin or PC-ASA in the same formulation. If without an aspirin component, a non-enteric, enteric, or partially enteric formulation of aspirin or active derivative (PC-ASA, PL2200, PA8140, or PA32540) could be taken orally the same day or every other day separately or separately from an oral/rectal dosage kit.

An embodiment exists where the aspirin or aspirin derivative is in a rectal suppository formulation with or without celecoxib, celecoxib analogue, PC-celecoxib, or PC-celecoxib analogue in the same formulation. If without, a non-enteric, enteric, or partially enteric formulation of celecoxib, celecoxib analogue, PC-celecoxib, or PC-celecoxib analogue could be taken orally the same day or every other day separately or separately from an oral/rectal dosage kit.

In all of the above embodiments, a non-enteric formulation may contain a film coating or other substances to improve the appearance and/or taste and/or to decrease absorption in the mouth, pharynx or esophagus as long as the non-enteric formulation absorption primarily occurs in the gastric and/or proximal small intestinal area. The film coating or other substances may also enhance the bioavailability and/or improve the stability of the formulation or perform other functions.

Both the enteric and non-enteric formulations may also be a controlled release preparation as long as the enteric formulation is primarily absorbed in the small intestine and/or colon and the non-enteric formulation is primarily absorbed in the gastric and/or proximal small intestinal area. Such a controlled release formulation may utilize medicated microspheres, nanospheres, polymer matrices, and/or other controlled release technology.

The controlled release and/or enteric/partially enteric embodiments may exist in one capsule of a capsule-in-capsule technology or within any part of the aspirin or aspirin derivative product (interior, inner wall of gelcap, middle of gelcap wall, coating exterior of gelcap with one or multiple layers, or exist separately within the self-emulsifying drug delivery system or tablet.

An embodiment exists where naproxen or PC-naproxen is substituted for the celecoxib, celecoxib analogue, PC-celecoxib, or PC-celecoxib analogue above. Naproxen has a reversible anti-platelet effect.

An embodiment exists where ibuprofen or PC-ibuprofen ("Zavryl") is substituted for the celecoxib, celecoxib analogue, PC-celecoxib, or PC-celecoxib analogue. However, in these embodiments care must be taken so that the aspirin or PC-ASA/PL2200 is taken or absorbed prior to the ibuprofen and that ibuprofen or PC-ibuprofen is not taken or absorbed from 8 hours before to about 30 minutes after the aspirin or aspirin derivative. Ibuprofen has a reversible anti-platelet effect that is known to interfere with the irreversible anti-platelet effect of aspirin.

An embodiment exists where another coxib, PC-coxib, conventional NSAID or PC-NSAID that does not interfere with aspirin's anti-platelet effect is substituted for the celecoxib, celecoxib analogue, PC-celecoxib, or PC-celecoxib analogue above. Non-coxib examples are diclofenac, meloxicam, sulindac, ketorolac, and acetaminophen.

Thus, embodiments of the sequential administration of partitioned absorption aspirin or active aspirin derivative and cox-2 inhibitor are disclosed. The implementations described above and other implementations are within the scope of the following claims. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of treating or prophylactically treating a patient for acute pain, fever, dysmenorrhea, acute migraine, prevention of migraine in a time window, or prevention of intra-abdominal adhesions comprising giving the patient a single dosage unit having no outer enteric coating and having partitioned sequential bioabsorption, the single dosage unit consisting essentially of a combination of a non-enteric aspirin or active aspirin derivative for rapid onset of action and absorption in a gastric area, or a duodenal area or both areas to provide anti-platelet effect, wherein the non-enteric aspirin or active aspirin derivative consists of acetylsalicylic acid or any of its active derivatives that can release salicylate in vivo and pharmaceutically acceptable amounts of inert fillers and binders; and a COX-2 inhibitor, wherein the COX-2 inhibitor has an enteric coating selected from one or more coatings comprising polymethacrylates, cellulose ester polymers, cellulose acetate trimellitate, hydroxypropyl methyl cellulose phthalate, hydroxypropyl methyl cellulose acetate succinate, polyvinyl derivatives, methacrylic acid copolymers, acrylic copolymers, or a mixture of sodium alginate and aqueous ammonium salt in shellac for sequential separation of the bioabsorption of the aspirin or active aspirin derivative from the bioabsorption of the COX-2 inhibitor and to deliver the COX-2 inhibitor in the patient's small intestine or colon for improved absorption and bioavailability of the COX-2 inhibitor and delayed distal release.

2. The method of claim 1, wherein bioabsorption of the COX-2 inhibitor occurs in the small intestine.

3. The method of claim 1, wherein the administering of the aspirin or active aspirin derivative and the COX-2 inhibitor is short-term.

4. The method of claim 1, wherein the administering of the aspirin or active derivative of aspirin and the COX-2 inhibitor is periodic.

5. The method of claim 1, wherein the aspirin or active derivative of aspirin comprises at least one of ASA, PC-ASA, PL2200, PA8140, and PA32540.

6. The method of claim 1, wherein the COX-2 inhibitor comprises celecoxib, celecoxib analogue, PC-celecoxib, or PC-celecoxib analogue.

7. The method of claim 1, wherein the coating is pH-sensitive, time-sensitive, and/or microflora-activated.

8. The method of claim 1, wherein the coating is methacrylic acid/ethyl acrylate copolymers, cellulose acetate phthalate, or polyvinyl acetate phthalate.

9. The method of claim 1, wherein the coating is aqueous-based or solvent-based.

10. The method of claim 1, wherein the coating is present in a range of 10-50 wt % of the coated COX-2 inhibitor.

11. A method of treating or prophylactically treating a patient for osteoarthritis, other arthritides, subacute and chronic pain, prophylaxis of subacute or chronic migraine, cancer treatment, and prevention or treatment of pre-cancerous intestinal polyps, or familial adenomatous polyposis comprising giving the patient a single dosage unit having no outer enteric coating and having partitioned sequential bioabsorption, the single dosage unit consisting essentially of a combination of a non-enteric aspirin or active aspirin derivative for rapid onset of action and absorption in a gastric area, or a duodenal area or both areas to provide anti-platelet effect, wherein the non-enteric aspirin or active aspirin derivative consists of acetylsalicylic acid or any of its active derivatives that can release salicylate in vivo and pharmaceutically acceptable amounts of inert fillers and binders; and a COX-2 inhibitor, wherein the COX-2 inhibitor has an enteric coating selected from one or more coatings comprising polymethacrylates, cellulose ester polymers, cellulose acetate trimellitate, hydroxypropyl methyl cellulose phthalate, hydroxypropyl methyl cellulose acetate succinate, polyvinyl derivatives, methacrylic acid copolymers, acrylic copolymers, or a mixture of sodium alginate and aqueous ammonium salt in shellac for sequential separation of the bioabsorption of the aspirin or active aspirin derivative from the bioabsorption of the COX-2 inhibitor and to deliver the COX-2 inhibitor in the patient's small intestine or colon for improved absorption and bioavailability of the COX-2 inhibitor and delayed distal release.

12. A method of treating or prophylactically treating a patient for dysmenorrhea, prevention of dysmenorrhea, menstrual or pre-menstrual migraine, prevention of menstrual or pre-menstrual migraine, prevention or treatment of dysmenorrhea and menstrual or pre-menstrual migraine in patients with both conditions, or prevention or treatment of migraine in a patient with recurring time windows where there is a need to be free of migraine symptoms during the time windows comprising giving the patient a single dosage unit having no outer enteric coating and having partitioned sequential bioabsorption, the single dosage unit consisting essentially of a combination of a non-enteric aspirin or active aspirin derivative for rapid onset of action and absorption in a gastric area, or a duodenal area or both areas to provide anti-platelet effect, wherein the non-enteric aspirin or active aspirin derivative consists of acetylsalicylic acid or any of its active derivatives that can release salicylate in vivo and pharmaceutically acceptable amounts of inert fillers and binders; and a COX-2 inhibitor, wherein the COX-2 inhibitor has an enteric coating selected from one or more coatings comprising polymethacrylates, cellulose ester polymers, cellulose acetate trimellitate, hydroxypropyl methyl cellulose phthalate, hydroxypropyl methyl cellulose acetate succinate, polyvinyl derivatives, methacrylic acid copolymers, acrylic copolymers, or a mixture of sodium alginate and aqueous ammonium salt in shellac for sequential separation of the bioabsorption of the aspirin or active aspirin derivative from the bioabsorption of the COX-2 inhibitor and to deliver the COX-2 inhibitor in the patient's small intestine or colon for improved absorption and bioavailability of the COX-2 inhibitor and delayed distal release.

* * * * *